(12) United States Patent
Bischoff et al.

(10) Patent No.: US 6,813,521 B2
(45) Date of Patent: Nov. 2, 2004

(54) MEDICAL ELECTRICAL LEAD

(75) Inventors: Thomas C. Bischoff, Minneapolis, MN (US); Marc R. Helmick, Newton, MA (US); Kathryn R. Parsons, Fridley, MN (US); Bret R. Shoberg, Corcoran, MN (US); George M. Huepenbecker, Vadnais Heights, MN (US); Sandra F. Viktora, Coon Rapids, MN (US); James J. Snyder, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 363 days.

(21) Appl. No.: 10/124,777

(22) Filed: Apr. 17, 2002

(65) Prior Publication Data

US 2002/0193860 A1 Dec. 19, 2002

Related U.S. Application Data

(60) Provisional application No. 60/284,430, filed on Apr. 17, 2001.

(51) Int. Cl.[7] .............................................. A61N 1/05
(52) U.S. Cl. ........................ 607/122; 607/127; 600/375
(58) Field of Search ................................ 607/122, 119, 607/116, 123, 127; 600/373, 374, 375, 393

(56) References Cited

U.S. PATENT DOCUMENTS

| | | | |
|---|---|---|---|
| 4,106,512 A | 8/1978 | Bisping | 128/418 |
| 4,217,913 A | 8/1980 | Dutcher | 128/785 |
| 4,311,153 A | 1/1982 | Smits | 128/785 |
| 5,231,996 A | 8/1993 | Bardy et al. | 128/785 |
| 5,246,014 A | 9/1993 | Williams et al. | 607/122 |
| 5,336,253 A | 8/1994 | Gordon et al. | 607/122 |
| 5,342,414 A | 8/1994 | Mehra | 607/127 |
| 5,425,755 A * | 6/1995 | Doan | 607/119 |
| 5,456,707 A * | 10/1995 | Giele | 607/127 |
| 5,534,022 A | 7/1996 | Hoffmann et al. | 607/122 |
| 5,584,873 A | 12/1996 | Shoberg et al. | 607/122 |
| 5,716,390 A * | 2/1998 | Li | 607/127 |
| 5,760,341 A | 6/1998 | Laske et al. | 174/126.2 |
| 5,837,006 A | 11/1998 | Ocel et al. | 607/127 |
| 5,948,015 A | 9/1999 | Hess et al. | 607/127 |
| 6,016,436 A * | 1/2000 | Bischoff et al. | 600/374 |
| 6,018,683 A * | 1/2000 | Verness et al. | 607/122 |
| 6,038,463 A * | 3/2000 | Laske et al. | 600/374 |
| 6,327,498 B1 | 12/2001 | Kroll | 607/4 |

* cited by examiner

Primary Examiner—Kennedy Schaetzle
(74) Attorney, Agent, or Firm—Michael C. Soldner; Girma Wolde-Michael

(57) ABSTRACT

A medical electrical lead is provided that is readily manufactured using a minimal number of parts, has a reduced size and improved reliability during implantation and extraction. The lead includes a modular electrode head assembly that is joined to a lead body at a butt joint. The butt joint is stabilized in at least four possible ways: insulation tubing that spans the joint is bonded to the electrode head assembly; two cabled conductors extending the length of the lead body are coupled to the electrode head assembly; an electrode head alignment peg interlocks with and is bonded to the lead body; and a coil electrode is positioned across the butt joint on the outer diameter of the assembly and the lead body. The lead size is minimized by using a compact retraction stop mechanism, a low-friction, press-fit drive shaft seal, and a small diameter coiled conductor insulated by a thin-walled insulating tube.

13 Claims, 9 Drawing Sheets

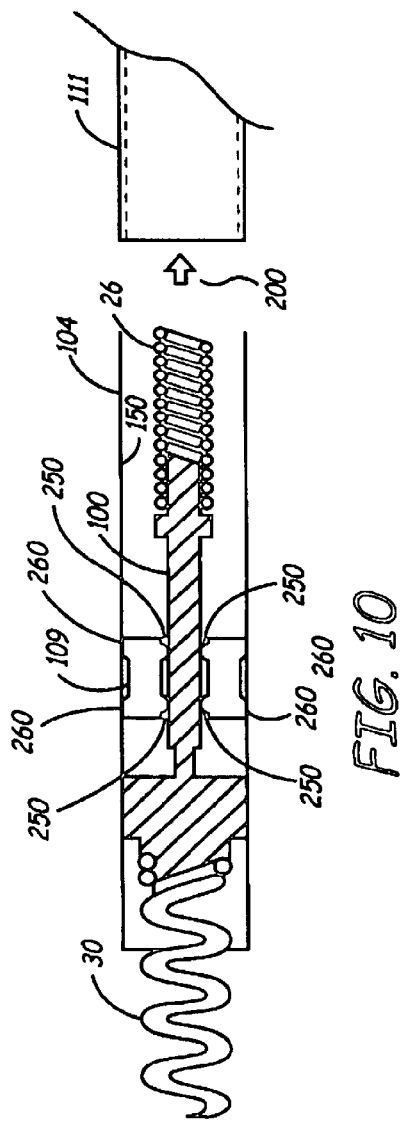
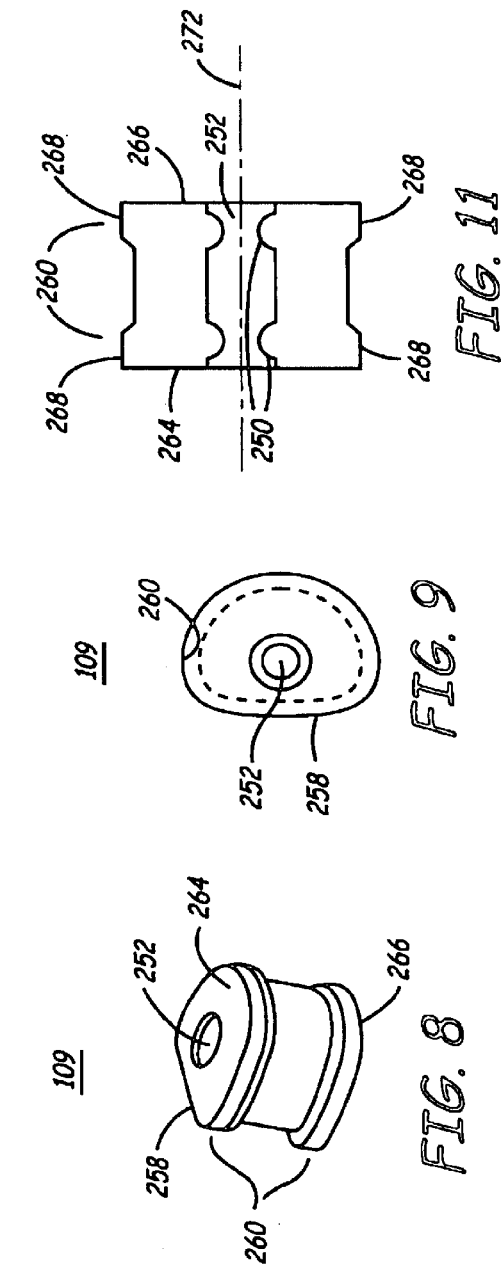

MEDICAL ELECTRICAL LEAD

REFERENCE TO PRIORITY APPLICATION

This application claims the benefit of U.S. Provisional Application No. 60/284,430, filed Apr. 17, 2001 entitled "MEDICAL ELECTRICAL LEAD", incorporated herein by reference in its entirety.

CROSS-REFERENCE TO RELATED APPLICATIONS

Cross-reference is hereby made to commonly assigned related U.S. Applications, filed concurrently herewith, Ser. No. 10/124,802, entitled "INSULATING MEMBER FOR A MEDICAL ELECTRICAL LEAD AND METHOD FOR ASSEMBLY"; 10/124,185, entitled "DRIVE SHAFT SEAL FOR A MEDICAL ELECTRICAL LEAD"; 10/124,530, entitled "IMPLANTABLE MEDICAL LEAD HAVING A RETRACTION STOP MECHANISM"; and 10/124,160, entitled "APPARATUS FOR TRANSFERRING TRACTION FORCES EXERTED ON AN IMPLANTABLE MEDICAL LEAD".

FIELD OF THE INVENTION

The present invention relates to a medical electrical lead, and, more specifically, relates to an implantable medical lead system that is readily manufactured with improved reliability.

BACKGROUND OF THE INVENTION

A wide assortment of automatic, implantable medical devices (IMDs) are presently known and in commercial use. Such devices include cardiac pacemakers, cardiac defibrillators, cardioverters, neurostimulators, and other devices for delivering electrical signals to a portion of the body and/or receiving signals from the body. Pacemakers, for example, are designed to operate so as to deliver appropriately timed electrical stimulation signals when needed, in order to cause the myocardium to contract or beat, and to sense naturally occurring conduction signals in the patient's heart.

Devices such as pacemakers, whether implantable or temporary external type devices, are part of a system for interacting with the patient. In addition to the pacemaker device, which typically has some form of pulse generator, a pacing system comprises one or more leads for delivering generated stimulation pulses to the heart and for sensing cardiac signals and delivering sensed signals from the heart back to the pacemaker. As is known, pacemakers can operate in either a unipolar or bipolar mode, and can pace the atria or the ventricles. Unipolar pacing requires a lead having only one distal electrode for positioning in the heart, and utilizes the case, or housing of the implanted device as the other electrode for the pacing and sensing operations. For bipolar pacing and sensing, the lead typically has two electrodes, a tip electrode disposed at the distal end of the lead, and a ring electrode spaced somewhat back from the distal end. Each electrode is electrically coupled to a conductive cable or coil, which carries the stimulating current or sensed cardiac signals between the electrodes and the implanted device via a connector.

Combination devices are available for treating cardiac arrhythmias that are capable of delivering electrical shock therapy for cardioverting or defibrillating the heart in addition to cardiac pacing. Such a device, commonly known as an implantable cardioverter defibrillator or "ICD", uses coil electrodes for delivering high-voltage shock therapies. An implantable cardiac lead used in combination with an ICD may be a quadrapolar lead equipped with a tip electrode, a ring electrode, and two coil electrodes. A quadrapolar lead normally requires four conductors extending the length of the lead body in order to provide electrical connection to each electrode, potentially resulting in a substantial increase in lead body diameter.

Other leads used with ICDs may be tripolar or bipolar. A tripolar lead that is also known as a "dedicated bipolar" lead is configured with a tip electrode, a ring electrode and a coil electrode. The tip and ring electrodes serve as a bipolar sensing pair. The coil electrode serves as the defibrillation electrode, and the tip electrode serves as the pacing electrode. An "integrated bipolar" lead, also used with ICDs, is configured with a tip electrode and a coil electrode but no ring electrode. The tip and coil electrodes serve as a bipolar pair for sensing and each serve individually as unipolar pacing and defibrillation electrodes, respectively. Each of these types of leads has different advantages related to the size of the lead, the location of the electrodes after implantation, and the characteristics of the sensed cardiac signals.

In order to work reliably, cardiac leads need to be located at a targeted cardiac tissue site in a stable manner. One common mechanism for securing an electrode position is the use of a rotatable fixation helix. The helix exits the distal end of the lead and can be screwed into the body tissue. The helix itself may serve as an electrode or it may serve exclusively as an anchoring mechanism to locate an electrode mounted on the lead adjacent to a targeted tissue site. The fixation helix may be coupled to a drive shaft that is further connected to a coiled conductor that extends through the lead body as generally described in U.S. Pat. No. 4,106,512 to Bisping et al. A physician may rotate the coiled conductor at its proximal end to cause rotation of the fixation helix via the drive shaft. As the helix is rotated in one direction, it is secured in the cardiac tissue. Rotation in the opposite direction removes the helix from the tissue to allow for repositioning of the lead at another location.

One problem that can arise with the use of a fixation helix is over-retraction of the helix during lead repositioning. Repositioning of the lead may be required during an implant procedure if poor electrical contact is made with the targeted cardiac tissue, resulting in higher than desired stimulation thresholds or poor sensing. The physician must retract the helix by applying turns to the coiled conductor in the appropriate direction. The physician may not have tactile feedback or fluoroscopic image indicating when the helix has dislodged from the heart tissue and is fully retracted. In many cases, the physician will perform additional turns of the coiled conductor in order to ensure the helix is safely removed from the heart tissue before applying tension to the lead to relocate it. Excessive turns, however, can cause deformation of the fixation helix rendering it unusable. In such cases, the lead must then be removed and replaced by a new lead.

To address the problem of over-retraction, a retraction stop mechanism may be provided within the distal lead head. An exemplary retraction stop mechanism that includes a fixed stop formed of a plurality of fixed cam and axial stop surfaces and a movable stop formed of a like plurality of rotatable cam and axial stop surfaces is disclosed in U.S. Pat. No. 5,837,006 to Ocel et al.

When using a lead having an open tip to allow for advancement and retraction of a fixation helix, it is desirable to prevent the ingress of body fluids into the lead body. Blood or other body fluids entering the lead body can create a pathway for infection, a serious complication with implantable devices. Furthermore, the entrance of blood into the lumen of a lead body can interfere with the insertion of a stylet, used for lead positioning during implantation, and with the final connection of the lead to an implantable medical device.

Methods for sealing the distal end of the lead body while still allowing a coiled conductor and drive shaft to rotate for advancing or retracting a fixation helix are known. One method is to provide a sealing membrane within the lumen of the distal lead tip. Reference is made to U.S. Pat. No. 4,311,153 issued to Smits. When the helix is advanced, the pointed tip of the fixation helix punctures the sealing membrane, which then provides a seal around the fixation helix. When used during implantation, multiple turns of the coil may be required in order to build up enough torque to overcome the friction encountered when rotating the helix through the membrane. The helix may not advance by the same amount with each turn applied to the coil. Therefore, the extension or retraction of the helix may be somewhat unpredictable. The punctured membrane may not always form a fluid-tight seal around the fixation helix. Another method for sealing the lumen of a medical lead involves positioning a sealing ring such that it encircles the drive shaft connected to the fixation helix. This type of seal may be maintained in a desired location by retainers mounted proximal and distal to the seal. Reference is made to U.S. Pat. No. 5,948,015 to Hess et al.

Infection or other changes in a patient's medical condition sometimes necessitates the removal of a chronically implanted lead. After a lead has been implanted in a patient's body for a period of time, fibrotic tissue growth typically encapsulates the lead, strongly adhering the lead to the surrounding tissue. Considerable traction applied to the proximal end of the lead may be necessary to pull the lead free. Reinforcement of some type extending along the lead body is beneficial in preventing breakage or partial disassembly of the lead during extraction. Several such reinforcement mechanisms are disclosed in U.S. Pat. No. 5,231,996 to Bardy et al.

In leads having an active fixation device, such as a fixation helix, the fixation device is generally housed in a relatively rigid electrode head member to provide support needed in securing the fixation device within the body tissue. The rigid electrode head member is coupled to a lead body that is more flexible for allowing easier passage through the cardiovascular structures. To improve the extractability of a lead of this type, it is desirable to transfer tensile force directly to the relatively rigid electrode head.

In the context of implantable cardiac leads, cabled or stranded conductors in place of commonly used coiled conductors provide increased tensile strength. Exemplary cabled or stranded conductors are disclosed in U.S. Pat. No. 5,760,341 issued to Laske et al., and U.S. Pat. No. 5,246,014 to Williams et al. The improved tensile strength will exist substantially between the electrode and the connector that the cabled or stranded conductor is coupled between.

Pacemaker systems, as well as other medical devices such as those mentioned above, can utilize a wide variety of lead designs. Many considerations are taken into account when optimizing the design of a lead. For example, minimizing lead size is important since a smaller device is more readily implanted within the cardiac structures or coronary vessels of a patient. Electrical insulation between multiple conductors and their associated electrodes is crucial to providing the desired therapeutic effect of electrical stimulation. Moreover, providing features that make a lead easier to implant and extract allows the clinician to complete the associated surgical procedure more safely and in less time. Finally, an optimized lead design is ideally manufactured at a low cost using techniques that are relatively simple and easy to verify. The resulting product should be easy to test so that manufacturing defects can be detected prior to the implant of the device within a patient. What is needed, therefore, is an improved lead design that takes all of the foregoing factors into account, thereby providing a medical lead that can be safely and efficiently deployed, used, and, if necessary, extracted.

SUMMARY OF THE INVENTION

The present invention is directed to a medical electrical lead system that includes a lead body having a plurality of lead body lumens, and an electrode head assembly, fixedly engaged with the lead body, having an electrode head assembly lumen with an inner wall. The electrode head assembly lumen communicating with a first lead body lumen of the plurality of lead body lumens. A first conductor extends within the first lead body lumen and the electrode head assembly lumen, an insulating member, extending through the electrode head assembly lumen and the first lead body lumen, electrically isolates the first conductor, and a drive shaft extends through the first lead body lumen and the electrode head assembly lumen. A sealing member has an outer diameter corresponding to the inner wall of the electrode head assembly lumen. The sealing member has an inner lumen that receives the drive shaft, an outer sealing member fixedly engaged with the inner wall of the electrode head assembly, and an inner sealing member engaged with the drive shaft to provide a low friction seal. A first electrode is electrically coupled to the first conductor by the drive shaft. An engaging member is positioned along the drive shaft and has a front surface. The medical electric lead system includes a flange portion that extends along the front surface of the engaging member and a retraction flange, wherein rotation of the drive shaft causes the flange portion to engage the retraction flange so that rotation of the drive shaft is absorbed by the first conductor. A second conductor extends within a second lead body lumen of the plurality of lead body lumens, and a second electrode, positioned along the electrode head assembly, has a deformation coupling the second electrode to the second conductor and transferring traction forces applied to the lead body to the electrode head assembly. A third electrode extends along the electrode head assembly and the lead body, a third conductor extends within a third lead body lumen of the plurality of lead body lumens, and an attachment member couples the third electrode and the third conductor and transfers traction forces applied to the lead body to the electrode head assembly.

BRIEF DESCRIPTION OF THE DRAWINGS

FIG. 8 is a perspective view of a drive shaft seal according to the present invention.

FIG. 9 is a sectional view of a drive shaft seal according to the present invention;

FIG. 10 is a plan view of a drive shaft and a drive shaft seal used in assembling a distal end of the lead, according to the present invention;

FIG. 11 is a side, cut-away view of a drive shaft seal according to the present invention;

DETAILED DESCRIPTION OF THE INVENTION

Figure 1:
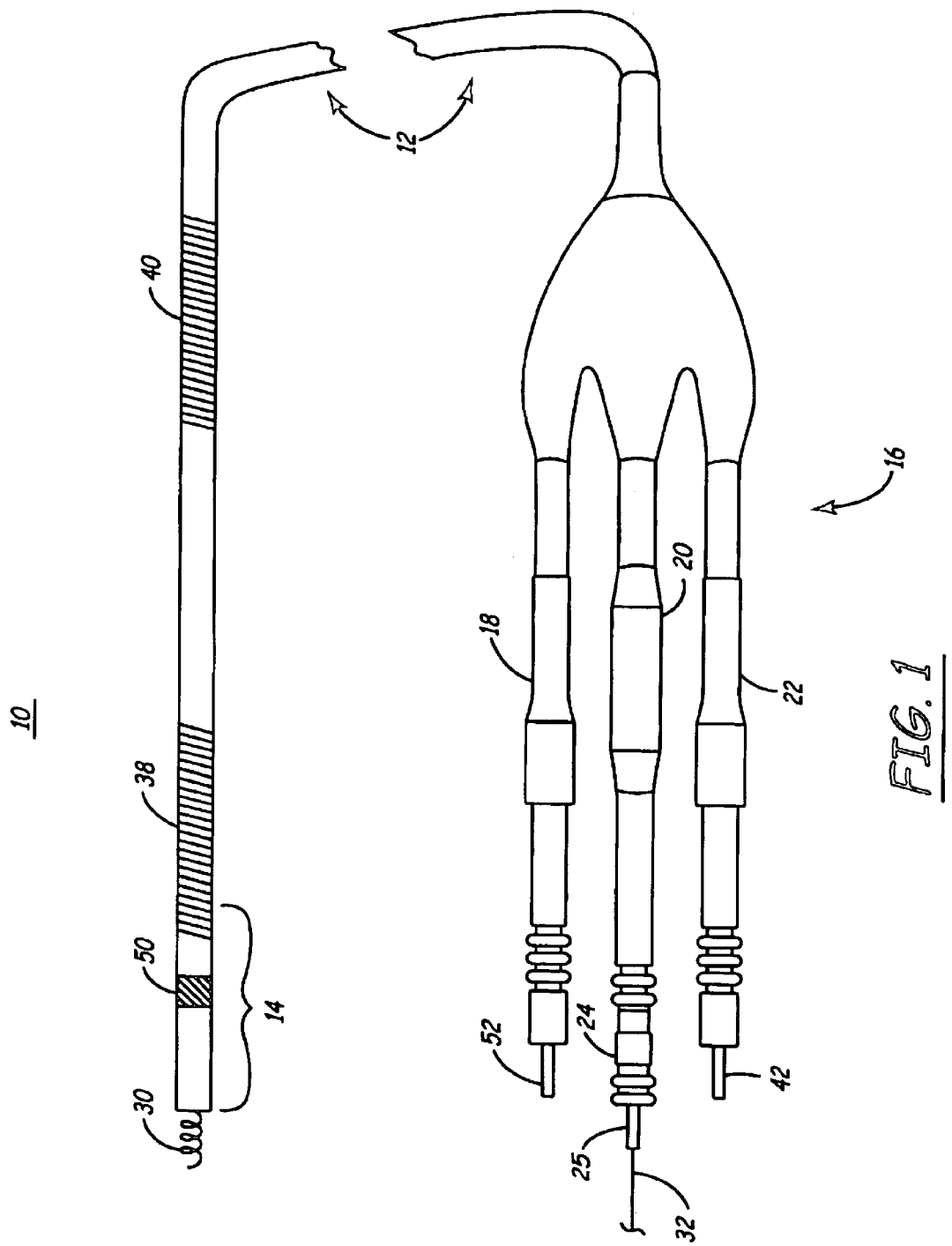
FIG. 1 is a plan view of an implantable cardiac lead utilized in accordance with the present invention.

FIG. 1 is a plan view of an implantable cardiac lead that may be used in accordance with the present invention, embodied as a transvenous cardiac defibrillation lead. As illustrated in FIG. 1, a lead 10 includes an elongated lead body 12 having a connector assembly 16 at a proximal end of the lead 10 for connecting to an implantable device, and an electrode head assembly 14 at a distal end of the lead 10 for carrying one or more electrodes. Lead 10 is shown as a quadrapolar lead including, at or near the distal end, a helical tip electrode 30, a ring electrode 50, a right ventricular (RV) defibrillation coil 38 and a superior vena cava (SVC) defibrillation coil 40. The helical tip electrode 30 and ring electrode 50 may be utilized to sense cardiac signals and/or deliver pacing pulses to a patient. One of the defibrillation coils 38 or 40 serves as the cathode while the other serves as the anode during delivery of a defibrillation shock to a patient as a result of a detected tachycardia or fibrillation condition.

The lead body 12 takes the form of an extruded tube of biocompatible plastic such as silicone rubber. Multiple lumens located within the lead body 12, carry four insulated conductors from the connector assembly 16 to the corresponding electrodes 30, 50, 38 and 40 located at or near the distal end of the lead 10. The multi-lumen lead body 12 may correspond generally to that disclosed in U.S. Pat. No. 5,584,873 issued to Shoberg et al., incorporated herein by reference in its entirety. Three of the insulated conductors carried by lead body 12 are stranded or cabled conductors, each electrically coupled to one of the ring electrode 50, RV coil 38 and SVC coil 40. The cabled conductors may correspond generally to the conductors disclosed in U.S. Pat. No. 5,246,014, issued to Williams et al., incorporated herein by reference in its entirety. A fourth, coiled conductor extends the length of the lead body 12 and is coupled to the helical tip electrode 30.

In this embodiment, the helical tip electrode 30 functions as an electrode for cardiac pacing and/or sensing and as an active fixation device for anchoring the lead 10 in a desired position. In other embodiments that may employ aspects of the present invention, a helical tip may function only as an active fixation device. Reference is made to U.S. Pat. No. 4,217,913 to Dutcher, incorporated herein by reference in its entirety. Therefore, the helical tip electrode 30 may also be referred to herein as a "fixation helix."

The connector assembly 16 has multiple connector extensions 18, 20, and 22 arising from a trifurcated connector sleeve, typically formed of silicone rubber. The connector extensions 18, 20, and 22 couple the lead 10 to an implantable medical device such as an implantable cardioverter defibrillator (ICD).

Connector extension 20 is shown as a bi-polar connector including a connector ring 24 and a connector pin 25. Connector extension 20 houses the cabled conductor that is electrically coupled to the connector ring 24 at its proximal end and to the ring electrode 50 at its distal end. The connector extension 20 also houses the coiled conductor that is electrically coupled to the connector pin 25 and extends to the tip electrode 30. During a lead implant or explant procedure, rotation of the connector pin 25 relative to the connector assembly 16 causes corresponding rotation of the coiled conductor and advancement or retraction of the helical tip electrode 30 in the fashion generally described in U.S. Pat. No. 4,106,512 to Bisping et al., incorporated herein by reference in its entirety. By advancing the tip electrode 30, the electrode 30 can be actively fixed in cardiac tissue. A stylet 32 may be advanced within an inner lumen of the coiled conductor to the distal end of the lead 10 to aid in lead placement during an implant procedure.

The connector extension 18 carries a single connector pin 52 that is electrically coupled to an insulated cable extending the length of the lead body 12 and electrically coupled to the RV coil 38. The connector extension 22 carries a connector pin 42 that is electrically coupled to a respective insulated cable that is further coupled to the SVC coil 40.

Figure 2:
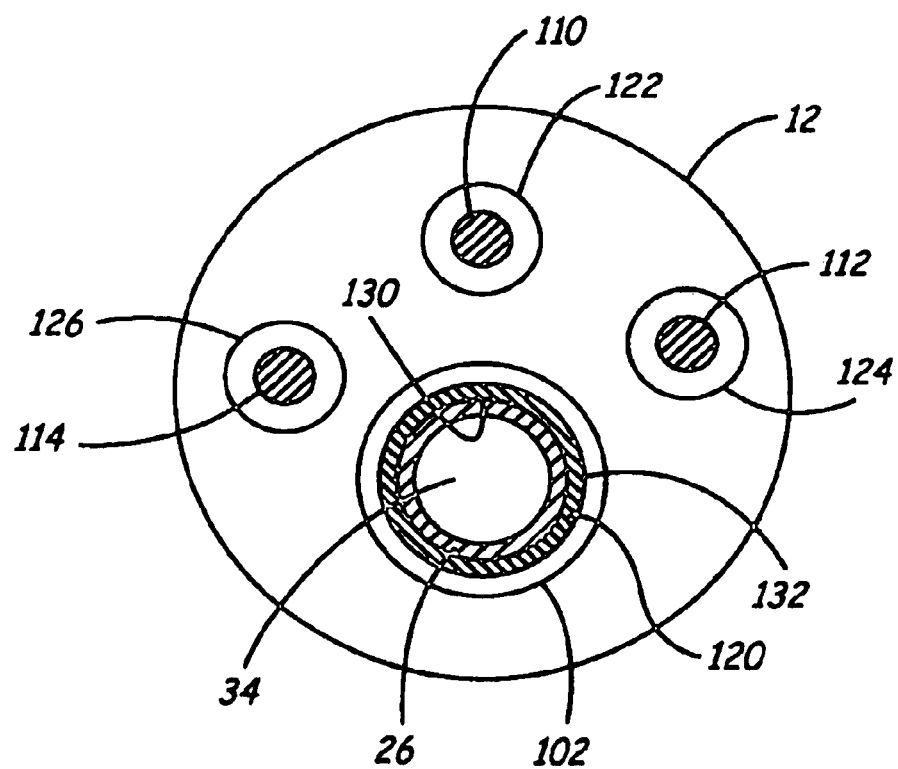
FIG. 2 is a sectional view of a multi-lumen lead body of the lead shown in FIG. 1.

FIG. 2 is a cross-sectional view of a multi-lumen lead body of the lead of FIG. 1. As illustrated in FIG. 2, the lead body 12 includes four lumens 102, 122, 124, and 126. Lumen 102 carries the coiled conductor 26 that is coupled to the helical tip electrode 30. In accordance with the present invention, the conductor 26 is shown surrounded by insulation tubing 120. A stylet 32 may be advanced within the lumen 34 of the coiled conductor 26. Lumen 122 carries an insulated cable 110 that is electrically coupled at a proximal end to the connector ring 24 and at a distal end to the ring electrode 50. Lumen 124 carries an insulated cable 112 that is electrically coupled at a proximal end to the connector pin 52 and at a distal end to the RV coil 38. Lumen 126 carries an insulated cable 114 that is electrically coupled at a proximal end to the connector pin 42 and at a distal end to the SVC coil 40.

Figure 3:
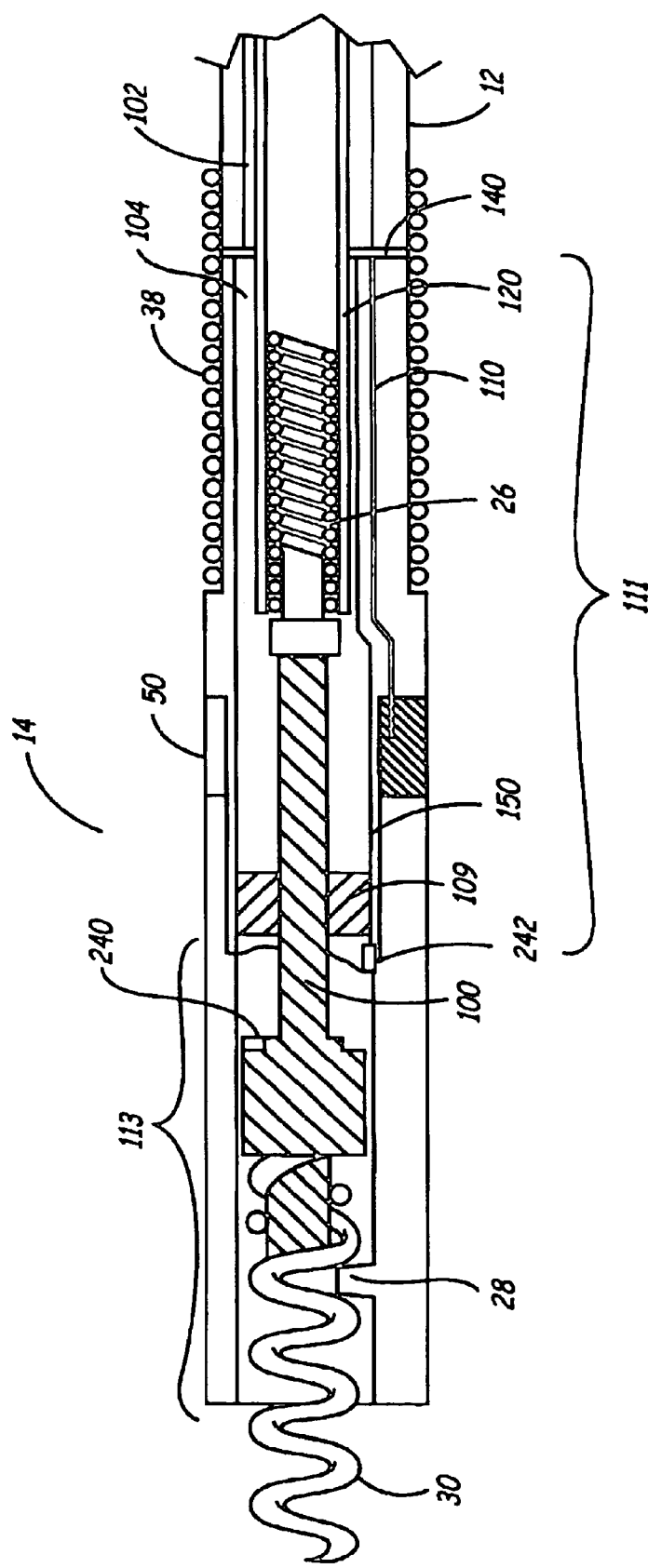
FIG. 3 is a side, cut-away view of a distal end of the lead shown in FIG. 1.

FIG. 3 is a side cutaway view of the distal end of the lead 10 showing a detailed view of the electrode head assembly 14 and the electrodes 30, 50 and 38. The molded, tubular electrode head assembly 14 includes two members, a distal electrode head assembly 113 and a proximal electrode head assembly 111. The distal and proximal electrode head assemblies 113 and 111 are preferably formed from a relatively rigid biocompatible plastic. For example, assemblies 113 and 111 may be fabricated from molded polyurethane. The proximal electrode head assembly 111 is coupled to the multi-lumen lead body 12, typically formed from a relatively more compliant plastic such as silicone rubber, at a joint 140. The lumen 104 within the proximal electrode head assembly 111 communicates with the lumen 102 within the lead body 12 for carrying the coiled conductor 26 extending between the tip electrode 30 and the connector ring 24. In FIG. 3, the ring electrode 50 is shown coupled to the cable 110, and the RV coil 38 is shown positioned on the outer diameter of the proximal electrode head assembly 111 and the lead body 12.

FIG. 3 further shows the helical tip electrode 30 electrically coupled to the coiled conductor 26 via a drive shaft 100. One particular advantage of fabricating the electrode head assembly 14 from polyurethane components is that polyurethane components may be made transparent. This transparency allows for inspection of the weld that affixes helical tip electrode 30 to the distal end of the drive shaft 100 so that lead integrity is better verified. The electrode 30 and drive shaft 100 are preferably fabricated of a biocompatible metal such as platinum iridium alloy. The coiled conductor 26 extends to the proximal connector assembly 16. Rotation of the connector pin 25 at the proximal end of coiled conductor 26 causes corresponding rotation of the distal end of the coiled conductor 26 to, in turn, cause rotation of the drive shaft 100. This rotation results in extension or retraction of helical tip electrode 30. A guide 28 actuates the helical tip 30 as it is advanced or retracted. The lead 10 may include a drive shaft seal 109 encircling the drive shaft 100. The drive shaft seal 109, which may be formed of silicone or any other elastomer, is housed within the proximal electrode head assembly 111.

One problem with quadrapolar leads involves maintaining electrical isolation between the various electrodes and conductors in the system. For example, when delivering pacing pulses to a patient, current is ideally supplied via coiled conductor 26 and helical tip electrode 30 to body tissue surrounding the tip electrode 30. Most of this current then travels through the body tissue back to ring electrode 50 and is then carried back to the implantable device via the cable 110. However, if electrical isolation is not maintained between the coiled conductor 26 and the RV coil 38, current may travel from the RV coil 38 to the coiled conductor 26 when high-energy defibrillation shocks are delivered, potentially injuring tissue in contact with the helical tip electrode 30.

The current invention utilizes an insulating member, such as a thin insulation tube 120, to electrically isolate the coiled conductor 26 from RV coil 38 and ring electrode 50. The insulation tube 120 extends from the lumen 104 within the proximal electrode head assembly 111, through the lumen 102 within the lead body 12, to the connector assembly 16. The insulation tube 120 is preferably a polymer having a high dielectric strength such as PTFE or ethyl tetrafluoroethylene (ETFE). The properties of PTFE are particularly suited for functioning as the insulation tubing around coiled conductor 26 because PTFE can be made into a tube with a smaller diameter and thinner wall than other polymers, such as silicone rubber or urethane, allowing overall lead size to be minimized. Furthermore, the PTFE tubing provides a low-interference and low-friction interface with the coiled conductor 26, which must easily rotate within the insulation tube 120 in order to advance or retract the fixation helix 30.

As illustrated in FIGS. 2 and 3, an inner lumen 130 of insulation member tube 120 houses coiled conductor 26, and prevents current leakage between the coiled conductor 26, RV coil 38 and ring electrode 50. In a preferred embodiment of the invention, an outer surface 132 of the insulation tube 120 is bonded to an inner surface 134 of lumen 104 within the proximal electrode head assembly 111 using an epoxy, polyurethane or other adhesive. Urethane adhesive is preferred because it is readily applied using a solvent, making the manufacturing process more efficient. The outer surface 132 of the insulation tubing 120 is preferably etched to facilitate bonding with adjacent components, such as the inner surface 134 of lumen 104. Additionally, the polyurethane adhesive provides an improved bond between PTFE insulation tube 120 and the urethane walls surrounding the lumen 104 over silicone adhesives. The ability to form a complete seal further prevents current leakage between the distal end of coiled conductor 26, RV coil 38, and ring electrode 50.

By bonding the insulation tubing 120 to the proximal electrode head assembly 111, a modular lead design is possible in which the proximal electrode head assembly is joined to the lead body 12 at the butt joint 140 shown in FIG. 3.

Figure 4:
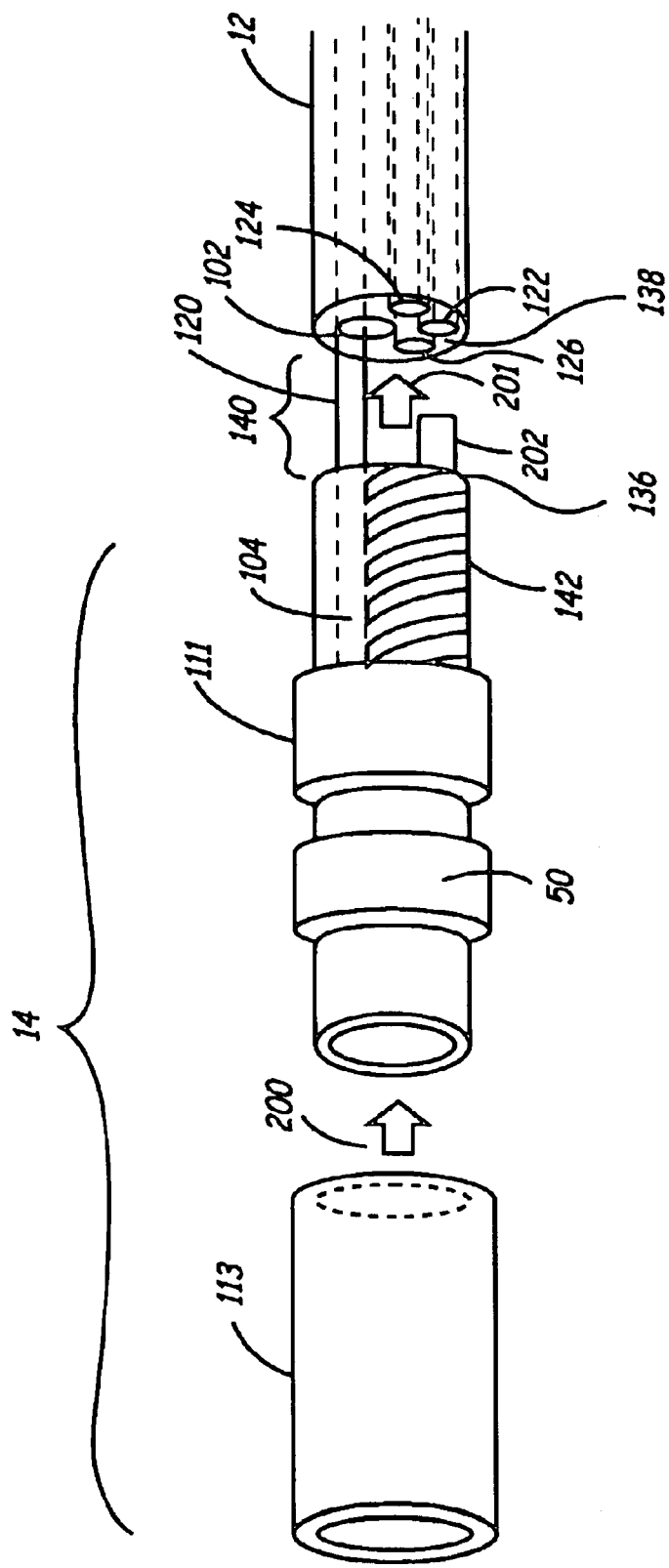
FIG. 4 is a perspective view of the modular components used in assembling the distal end of the lead shown in FIG. 3.

FIG. 4 is a perspective view illustrating the modularity that may be provided by the electrode head assemblies 111 and 113 and the multi-lumen lead body 12 with use of the insulation tubing 120. Arrows 200 and 201 show the manner in which the distal and proximal electrode head assemblies 113 and 111 are joined together and with lead body 12. According to one method of assembling this lead 10, the insulation tubing 120 may be inserted into lumen 104 of the proximal electrode head assembly 111 and bonded thereto using, for example, a urethane adhesive. Next, the unbonded proximal end of the insulation tubing 120 may be inserted into lumen 102 at the distal end of the lead body 12. A bonding process may then be utilized to bond a proximal end 136 of the proximal electrode head assembly 111 to a distal end 138 of the silicone lead body 12 at butt joint 140 so that the proximal end 136 is fixedly positioned adjacent to the distal end 138. For example, a silicone adhesive may be used to facilitate this bonding of the proximal end 136 to the distal end 138. The insulation tubing 120 provides mechanical stability, electrical isolation, added lead body strength, and improved flex life in the vicinity of the butt joint 140.

The assembly of lead 10 may also include bonding the RV coil 38 to an outer portion 140 of the lead body 12 and an outer portion 142 of the proximal electrode head assembly 111, as in the position shown in FIG. 3. The grooved area 142 of assembly 111 provides an adhesive grip and aids in holding the RV coil 38 in place. The placement of RV coil 38 across the butt joint 140 provides additional stability to the joint 140. The ring electrode 50 is captured in the position shown in FIG. 3 between the distal electrode head assembly 113 and the proximal electrode head assembly 111 after they are joined. The cabled conductor 110 coupled to the ring electrode 50 (FIG. 3) provides additional stress relief to the butt joint 140.

FIG. 4 further shows an optional electrode head peg 202 used in conjunction with lumen 126 to provide alignment of the proximal electrode head assembly 111 and the lead body 12 during the manufacturing process. As shown previously in FIG. 2, the lumen 126 houses the cable 114 (shown in FIG. 2) that extends from connector assembly 16 to the SVC coil 40. Distal to the SVC coil 40, the lumen 126 is empty, advantageously providing a port at the distal end of the lead body 12 in which to engage the electrode head peg 202. The electrode head peg 202 may be bonded within lumen 126 using an adhesive, preferably a silicone adhesive, to provide additional strength and strain relief to the butt joint 140.

The modular assembly provided by the embodiments of the invention described above provides several advantages. The assembly method allows the proximal and distal electrode head assemblies 111 and 113 to be manufactured separately and coupled to the lead body 12 later in the manufacturing process. The modular design makes the electrode head assemblies 111 and 113 easier to inspect and test, and also simplifies the lead assembly process. By utilizing the insulation tubing 120, a method for joining a polyurethane electrode head assembly 14 and a silicone lead body 12 in a stable, reliable manner can be realized without increasing the lead diameter at the joint or requiring difficult manufacturing processes. It may further be noted that the RV defibrillation coil 38 and the optional electrode head peg 202 provide additional strain relief at the butt joint 140.

FIG. 3 further shows the helical tip electrode 30 electrically coupled to the coiled conductor 26 via a drive shaft 100. The electrode 30 and drive shaft 100 are preferably fabricated of a biocompatible metal such as platinum iridium alloy. The coiled conductor 26 extends to the proximal connector assembly 16. Rotation of the connector pin 25 at the proximal end of coiled conductor 26 causes corresponding rotation of the distal end of the coiled conductor 26 to, in turn, cause rotation of the drive shaft 100. This rotation results in extension or retraction of helical tip electrode 30. A guide 28 actuates the helical tip 30 as it is advanced or retracted. The lead 10 may include a drive shaft seal 109 encircling the drive shaft 100. The drive shaft seal 109, which may be formed of silicone or any other elastomer, is housed within the proximal electrode head assembly 111.

According to the present invention, as illustrated in FIG. 3, the ring electrode 50 is coupled to the cable 110 via two deformations 220. During assembly, a tool is used to press the ring electrode 50 against the cable 110 creating indentations or crimp-like deformations 220, which ensure the electrical coupling of the ring electrode 50 to the cable 110. Ring electrode 50 is captured between the proximal and distal electrode head assemblies 111 and 113 when the assemblies 111 and 113 are bonded together. In this way, traction forces applied at the proximal lead end are transferred to the electrode head assembly 14 in part via the cable 110 that is coupled to the ring electrode 50 via deformations 220.

Figure 5:
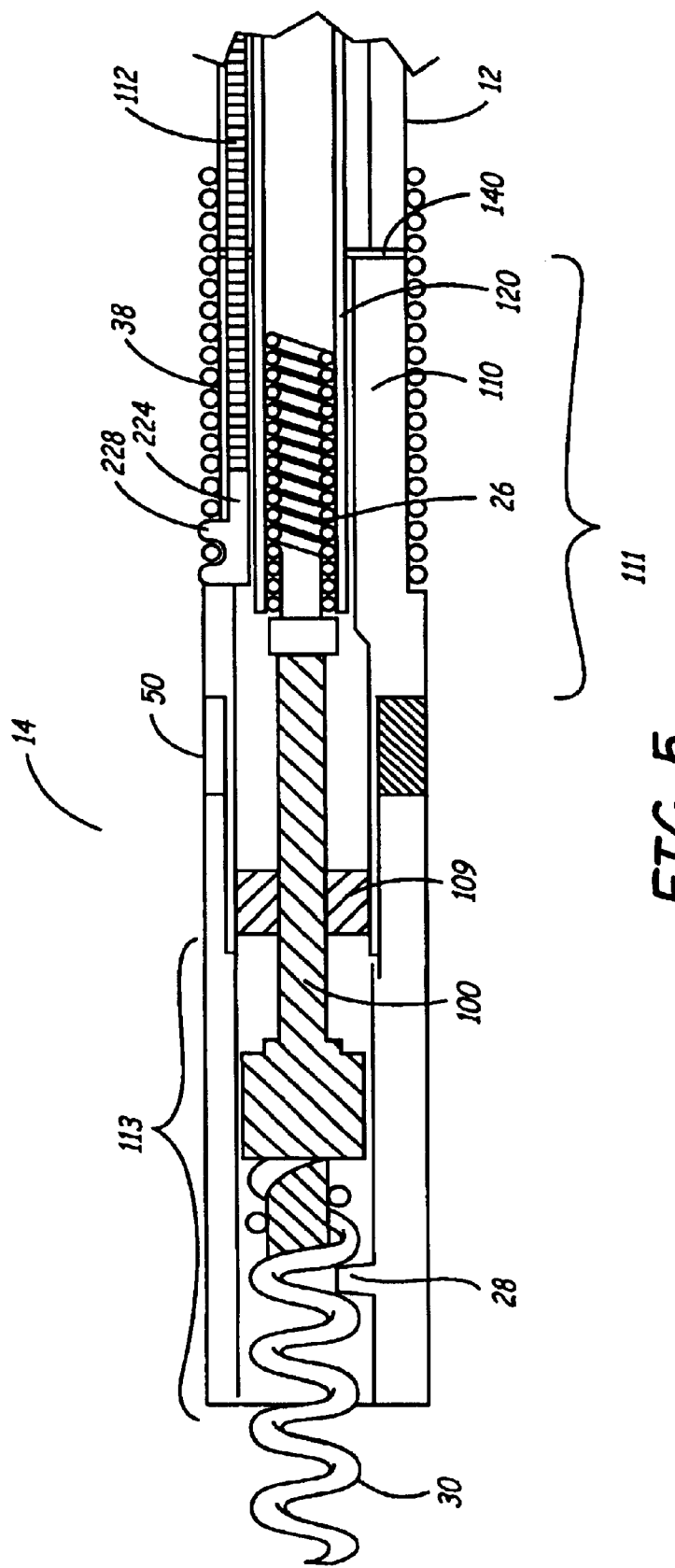
FIG. 5 is a side, cut-away view of the distal end of the lead shown in FIG. 1 showing a second cable connected to a coil electrode and the electrode head assembly.

As illustrated in FIGS. 3 and 5, the RV coil 38 is positioned on an outer surface 140 of the proximal electrode head assembly 111 and the lead body 12. As illustrated in FIG. 5, a cross-groove crimp sleeve, or attachment member 224, provides electrical connection of cable 112 to the RV coil 38 and mechanical connection to the proximal electrode head assembly 111. The attachment member 224 is fabricated of a conductive biocompatible metal such as titanium or platinum. The attachment member 224 provides a tubular portion for receiving the cable 112 and a groove, running perpendicular to the tubular portion, for receiving one or more coils of RV coil 38 in a manner as generally described in U.S. Pat. No. 5,676,694 to Boser et al., and in U.S. Pat. No. 6,016,436 to Bischoff et al., both patents incorporated herein by reference in their entirety.

Figure 6:
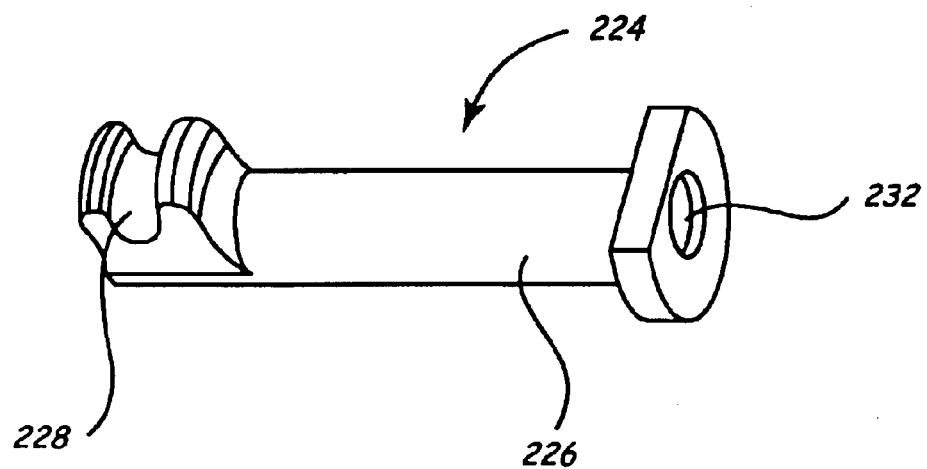
FIG. 6 is a perspective view of an attachment member used for interlocking with a coil electrode and a cable in a distal end of a lead according to the present invention.

FIG. 6 is a perspective view of an attachment member for interlocking with a coil electrode and a cable in a distal end of a lead, according to the present invention. As illustrated in FIG. 6, the attachment member 224 according to the present invention includes a cross-groove 228 for receiving one or more coils of RV coil 38 and a tubular receiving portion 226 having a lumen 232 for receiving the cable conductor 112. The RV coil 38 may be welded or brazed within the groove 228. Alternatively, this connection may be made by crimping or otherwise compressing the groove 228 around RV coil 38 to provide an electrical and mechanical coupling to the coil 38. The cable 112 may be coupled to the attachment member 224 by crimping the receiving portion 226, or staking, welding, brazing or otherwise mechanically and electrically coupling the cable 112 to the sleeve 224.

Figure 7:
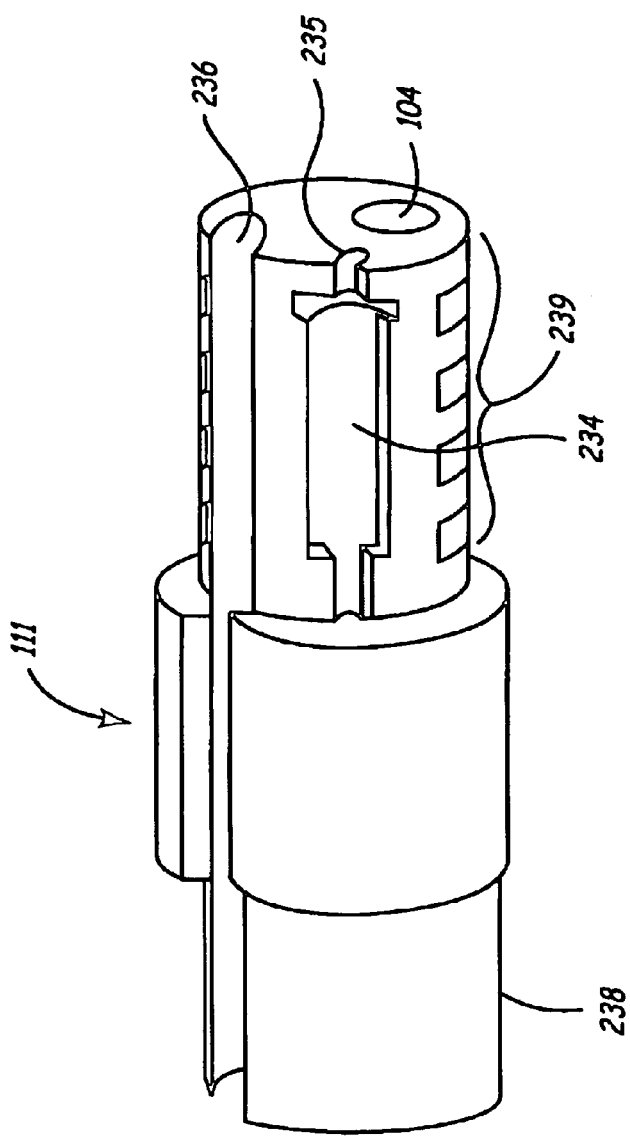
FIG. 7 is a perspective view of the electrode head assembly according to the present invention.

FIG. 7 is a perspective view of a proximal electrode head assembly according to the present invention. As illustrated in FIG. 7, the proximal electrode head assembly 111 includes a recess 234 for retaining the attachment member 224. The attachment member 224 is maintained within the recess 234 by a biocompatible plastic tube surrounding the proximal end 239 of the assembly 111. The RV coil 38 is positioned over the proximal end 239 with one or more coils interlocking with cross-groove 228 of the attachment member 224 (FIG. 6) residing in recess 234. A second recess 236 is provided for retaining the cable 110 that is coupled to ring electrode 50, which is positioned over the distal end 238 of the assembly 111. The deformations 220 (FIG. 3) electrically couple the ring electrode 50 to the cable 110 residing in recess 236 and thereby couple the cable 110 to the electrode head assembly 14 once the ring electrode 50 is captured between proximal and distal electrode head assemblies 111 and 113 as shown in FIG. 3.

In addition, as illustrated in FIG. 7, the recess 234 includes an opening so that once attachment member 224 is inserted within the recess 234, opening 235 is adjacent to the lumen 232 so that the cable conductor 112 is inserted within opening 235 and lumen 232 and positioned at the receiving portion 226.

Thus, two connections are provided to the electrode head assembly 14, one by the cable 110 residing in recess 236 coupled to ring electrode 50 and the other by the cable 112 interlocking with the attachment member 224 residing in recess 234. This double connection to the electrode head assembly from the cables 110 and 112, which extend proximally to connector assembly 16, provides improved tensile strength to lead 10 for better withstanding extraction forces applied during lead removal. Traction forces applied to the proximal end of lead 10 will be transferred via the cables 110 and 112 to the electrode head assembly 111, preventing separation of lead body 12 from the electrode head assembly 111 or other lead breakage. A redundant lead strengthening mechanism is provided by having two cable connections to the electrode head assembly 14 so that, should one connection fail, the remaining connection will prevail, thereby ensuring tensile integrity of the lead 10.

FIG. 8 is a perspective view of a drive shaft seal according to the present invention. As illustrated in FIG. 8, the drive shaft seal 109 includes two outer sealing rings 260 located substantially at each end of the seal 109. It is recognized that any number of outer sealing rings may be provided any where along the length of seal 109. These outer sealing rings 260 form a high-friction seal with the inner diameter of the electrode head assembly 14.

In particular, as illustrated in FIG. 8, an outer diameter 258 of the seal 109 has a "D" shape. This "D" shape, which is also shown by the sectional view of FIG. 9, matches a "D" shaped inner diameter of the electrode head assembly 14. The seal 109 has a circular inner lumen 252, through which the drive shaft 100 passes. According to the present invention, the particular shape of the outer diameter 258 may be of any shape that corresponds to the inner diameter of the electrode head assembly 14. Interference between the outer diameter 258 and the inner diameter of electrode head assembly 14 prevents shifting or rotation of the seal 109 relative to the electrode head assembly 14 when the drive shaft 100 is rotated within circular lumen 252. The outer sealing rings 260 are sized to provide a press fit so that the outer sealing rings 260 are fixedly engaged against an inner wall 150 of the lumen 104 of electrode head assembly 14, creating a seal along inner wall capable of withstanding pressures that may be typically encountered within the cardiovascular system.

FIG. 10 is a plan view of a drive shaft and a drive shaft seal used in assembling a distal end of the lead, according to the present invention. As illustrated in FIG. 10, the drive shaft seal 109 is positioned over the drive shaft 100 prior to welding the coiled conductor 26 to the proximal portion of the shaft 100. Then the proximal, non-welded end of the coiled conductor 26 is inserted in the tubular electrode head assembly 14 as indicated by the arrow 200. The coiled conductor 26 and the drive shaft 100 are advanced within the electrode head assembly 14 until the seal 109 is fit within the electrode head assembly 14, in a position as shown in FIG. 3. Because the drive shaft seal 109 is retained within the electrode head assembly 14 via a friction fit, assembling the lead 10 with the seal 109 does not require additional parts or bonding methods. As a result, fewer manufacturing faults occur during lead production, manufacturing cost is decreased, and the assembly process is made simpler.

FIG. 11 is a side, cut-away view of a drive shaft seal according to the present invention. As illustrated in FIG. 11, the shaft seal 109 according to the present invention includes two inner sealing rings 250 that flexibly conform to the drive shaft 100. The inner sealing rings 250 are shown located substantially at each end of the seal 109, but it is recognized that any number of sealing rings may positioned any where along the length of the seal 109 within the inner lumen 252. The inner sealing rings 250 are shown to be semi-circular in cross-section in FIG. 11, however the inner sealing rings 250 may be of any geometrical shape in cross-section, such as square, rectangular or otherwise, that still provides an acceptable sealing interface with the drive shaft 100. Likewise, the two outer sealing rings 260 are not limited to having the cross-sectional geometry illustrated in FIG. 11 but could have any geometrical shape that provides an acceptable sealing interface with the head electrode head assembly 14.

Because the inner sealing rings 250 provide a low friction seal when engaged against the drive shaft 100, the drive shaft 100 is allowed to rotate without encountering an undue amount of friction. As a result, the coiled conductor 26 used to rotate the drive shaft 100 may be constructed with smaller, more responsive coils. Smaller coil diameter results in an overall reduced lead body size. The low friction seal provided by the inner sealing rings 250 allows for the linear or near-linear transfer of torque from the proximal end of coiled conductor 26 to the helical tip 30, making helix extension easy to control, while stopping ingress of fluid within the lumen 104 electrode head assembly 14, while allowing rotation of the drive shaft 100 within the inner lumen 252.

As illustrated in FIGS. 8 and 11, drive shaft seal 109 includes a distal portion 264 and a proximal portion 266. According to the present invention, the drive shaft seal 109 is molded so that the outer sealing rings 260 are form with an outer edge 268 that is square, so that parting lines 270 corresponding to the distal portion 264 and the proximal portion 266 are perpendicular to an axis 272 extending through the inner lumen 252 of the drive shaft seal 109, and the mold used during the molding process is parted along the squared outer edge 268. As a result, the drive shaft seal 109 of the present invention provides a robust seal by avoiding potential breaks in the seal at the outer sealing rings 260.

In addition, inner sealing rings 250 of the drive shaft seal 109 of the present invention are positioned to be aligned with opposite positioned outer sealing rings 260. As a result, the drive shaft 100 exerts a force on the inner sealing rings 250 which is translated directly to the corresponding oppositely positioned outer sealing rings 260, while at the same time inner wall 150 of lumen 104 exerts a force on the outer sealing rings 260 which is translated directly to corresponding oppositely positioned inner sealing rings 250. As a result, localized pressure at the seal formed between the outer sealing rings 260 and the inner wall 150, and between the drive shaft 100 and the inner sealing rings 250 is stabilized, improving the seal formed by the inner sealing rings 250 and the outer sealing rings 260.

The drive shaft seal is formed from a resilient, supple material, preferably silicone rubber. The volume of the seal is made as large as possible within the available space of the electrode head assembly in order to increase the compliance of the seal and provide a tightly pressed fit within the electrode head assembly, thereby improving the effectiveness of the seal. A large surface area on the outer diameter of the seal provides interference with the adjacent electrode head assembly creating a high-friction fit that prevents shifting of the seal. A lower surface area on the inner diameter of the seal provides a low-friction interface with the drive shaft, allowing the shaft to easily rotate within the seal.

The present invention thus provides a reliable seal against body fluids in an implantable medical lead. The seal further provides a low-friction interface with a rotatable drive shaft such that less torque is needed to advance the helix than with prior known sealing methods. This low-friction interface allows predictable linear advancement of the fixation helix with each turn applied to a coiled conductor. The low-friction seal further allows the coiled conductor to be made from smaller coils, reducing overall lead size. The seal provided by the present invention is easy to assemble since no additional parts or bonding methods are required.

Figure 13:
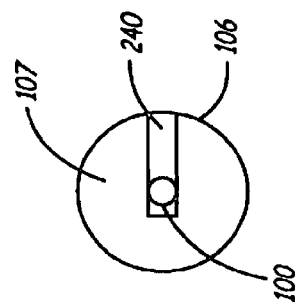
FIG. 13 is a planar view of a front surface of the retraction stop mechanism of FIG. 12.
Figure 12:
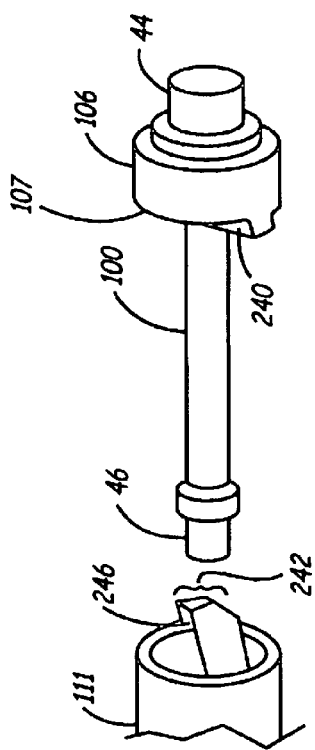
FIG. 12 is a perspective view of a retraction stop mechanism of an implantable cardiac lead according to the present invention.

FIG. 12 is a perspective view of a retraction stop mechanism of an implantable cardiac lead according to the present invention. FIG. 13 is a planar view of a front surface of the retraction stop mechanism of FIG. 12. As illustrated in FIG. 12, the drive shaft 100 includes a distal stem 44 for coupling to the helical tip electrode 30. A proximal stem 46 is provided for coupling to the coiled conductor 26. As illustrated in FIGS. 12 and 13, an axial stop surface, or flange portion 240 extends in a proximal direction from a front surface 107 of a movable stop, or engaging member 106, that is formed as a cylindrical body near the distal end of the drive shaft 100. The drive shaft 100 and engaging member 106 with the flange portion 240 may be machined as one component, eliminating additional parts, welding processes or weld inspections needed for providing a movable retraction stop.

As illustrated in FIGS. 3 and 12, the distal end of the proximal electrode head assembly 111 includes a fixed retraction flange 242 that includes an axial stop surface 246. The fixed retraction flange 242 is a distal protrusion positioned within the electrode head assembly 14. The electrode head assembly 14, including the fixed retraction flange 242 may be formed as a single, molded polyurethane component. Therefore, implementing the fixed retraction flange 242 in lead 10 does not require additional parts or bonding procedures during lead assembly.

Figure 14:
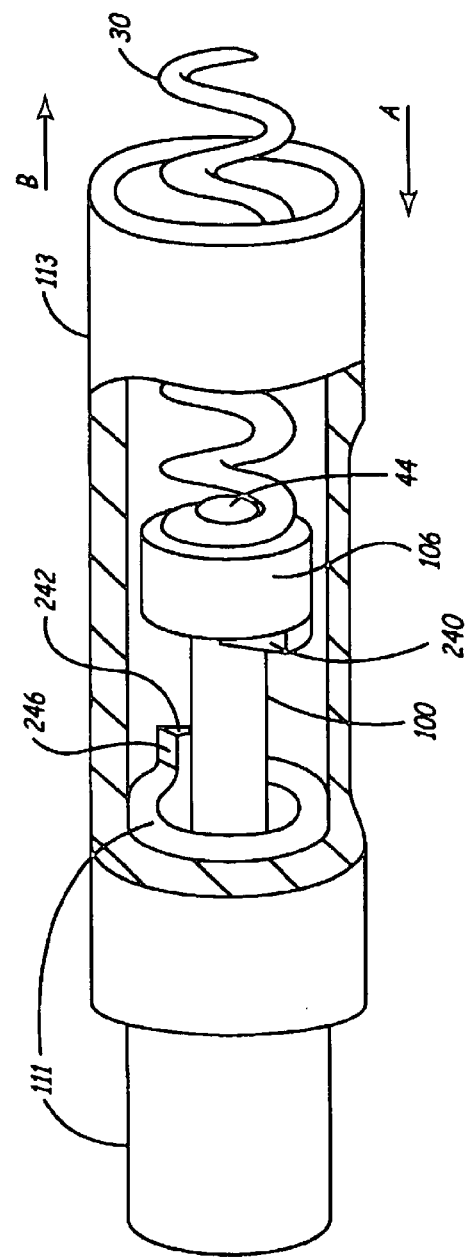
FIG. 14 is an enlarged, perspective, partially cut-away view of a retraction stop mechanism according to the present invention.

FIG. 14 is an enlarged, perspective, partially cut-away view of a retraction stop mechanism according to the present invention. As illustrated in FIGS. 3 and 14, as the connector pin 25 at the proximal end of coiled conductor 26 is rotated in a first, clockwise direction so as to retract the helical tip electrode 30, this rotation of the connector pin 25 in the first direction causes the drive shaft 100 to rotate in the first direction. As the drive shaft 100 rotates, the electrode 30 and the engaging member 106 are also rotated in the first direction. As the electrode 30 is rotated in the first direction, the electrode 30 advances through the guide 28, causing the electrode 30 to be advanced through the electrode head assembly 14 in a direction shown by arrow A, so as to be advanced towards the electrode head assembly 14, thereby retracting the electrode 30 from the cardiac tissue and within the electrode head assembly 14.

At the same time, the rotation of the drive shaft 100 in the first direction also causes the engaging member 106 to be rotated in the first direction, while at the same time, the movement of the electrode 30 through the guide 28 causes the engaging member 106 to also be advanced within the electrode head assembly 14 in the direction A. Furthermore, the rotation of the drive shaft 100 in the first direction results in the engaging member 106 being rotated about the drive shaft 100 so that as engaging member 106 advances in the direction A, the flange 240 engages against the fixed retraction flange 242 upon complete retraction of the helical tip electrode 30, so that the torque resulting from extra turns applied to the connector pin 25 after the helical tip electrode 30 is completely retracted within distal assembly 113 will, therefore, not be transmitted to the helical tip electrode 30. Rather, additional torque is absorbed by the coiled conductor 26. Deformation of the helical tip electrode 30 is thereby avoided, allowing repositioning of the lead 10.

As the connector pin 25 at the proximal end of coiled conductor 26 is rotated in a second, counterclockwise direction in order to advance of the helical tip electrode 30 within the cardiac tissue to secure the lead, this rotation of the connector pin 25 in the second direction causes rotation of the drive shaft 100 in the second direction. As the drive shaft 100 rotates, the electrode 30 and the engaging member 106 are also rotated in the second direction. As the electrode 30 is rotated in the second direction, the electrode 30 advances through the guide 28, causing the electrode 30, to be advanced through the electrode head assembly 14 in a direction shown by arrow B, away from the electrode head assembly 14, so that the electrode 30 is advanced outward from the distal end of the electrode head assembly 14 and is inserted within the cardiac tissue.

At the same time, the rotation of the drive shaft 100 in the second direction also causes the engaging member 106 to be rotated in the second direction, while at the same time, the movement of the electrode 30 through the guide 28 causes the engaging member 106 to also be advanced within the electrode head assembly 14 in the direction B. Furthermore, the rotation of the drive shaft 100 in the second direction results in the engaging member 106 being rotated about the drive shaft 100 so that as engaging member 106 advances in the direction B, the flange portion 240 disengages from against the fixed retraction flange 242. As a result, when the drive shaft 100 is rotated in the in the second direction, opposite the first direction, the retraction stop mechanism of the present invention does not prevent rotation of the engaging member 106, allowing advancement of the helical tip electrode 30 through the electrode head assembly 14 in the direction B.

According to the present invention, the flange 240 and the axial stop surface 246 are compact such that little space within the electrode head assembly 14 is required to provide a retraction stop mechanism. Furthermore, the fixed retraction flange 242 and the engaging member 106 have geometries that may be incorporated directly into the molded electrode head assembly 14 and the machined drive shaft 100, respectively, without requiring additional parts or bonding or welding procedures. The retraction stop mechanism of the present invention is advantageously located proximal to the stem 44 allowing the welded joint between the helical tip electrode 30 and the stem 44 to be easily inspected. Thus, the assembly procedures for a lead having a retraction stop mechanism in accordance with the present invention are kept simple and are easily verified, resulting in a more reliable lead.

Features included in the present invention provide a lead system manufactured from a minimal number of parts with a reduced size. Providing a small-diameter coiled conductor that easily rotates within a thin-walled insulation tube capable of transferring torque to the fixation helix in a linear way with the use of a low-friction seal minimizes the lead body diameter and improves lead performance. The seal is press fit, eliminating additional parts or bonding methods for retaining the seal in a correct position. Providing a retraction stop mechanism that does not require additional components and occupies a minimal amount of space within the distal lead end further minimizes lead size and eases manufacturing.

The lead described above with respect to the current inventive lead system is a quadrapolar high-voltage lead of the type that may be used in conjunction with an implantable cardioverter defibrillator. However, it will be understood by one skilled in the art that any or all of the inventive aspects described herein may be incorporated into other types of medical leads. For example, aspects included in the present invention for minimizing lead size and easing manufacturing methods may be implemented in a multipolar pacing lead, an integrated bipolar lead, or a dedicated bipolar lead. Aspects included in the present invention may therefore be incorporated in a lead having any combination of a tip electrode, one or more ring electrodes, or one or more coil electrodes for use in pacing, sensing, and/or shock delivery. Alternatively, drug-delivery or other electrical stimulation leads may employ aspects of the current inventive lead system for minimizing lead size, ensuring reliability, and simplifying assembly and testing methods. As such, the above disclosure should be considered exemplary, rather than limiting, with regard to the following claims.

We claim:

1. A medical electrical lead system, comprising:
    a lead body having a plurality of lead body lumens;
    an electrode head assembly, fixedly engaged with the lead body, having an electrode head assembly lumen with an inner wall, the electrode head assembly lumen communicating with a first lead body lumen of the plurality of lead body lumens;
    a first conductor extending within the first lead body lumen and the electrode head assembly lumen;
    an insulating member, extending through the electrode head assembly lumen and the first lead body lumen, electrically isolating the first conductor;
    a drive shaft extending through the first lead body lumen and the electrode head assembly lumen;
    a sealing member having an outer diameter corresponding to the inner wall of the electrode head assembly lumen, the sealing member having an inner lumen receiving the drive shaft, an outer sealing member fixedly engaged with the inner wall of the electrode head assembly, and an inner sealing member engaged with the drive shaft to provide a low friction seal;
    a first electrode electrically coupled to the first conductor by the drive shaft;
    an engaging member positioned along the drive shaft and having a front surface;
    a flange portion extending along the front surface of the engaging member;

a retraction flange, wherein rotation of the drive shaft causes the flange portion to engage the retraction flange so that rotation of the drive shaft is absorbed by the first conductor;

a second conductor extending within a second lead body lumen of the plurality of lead body lumens;

a second electrode, positioned along the electrode head assembly, having a deformation coupling the second electrode to the second conductor and transferring traction forces applied to the lead body to the electrode head assembly;

a third electrode extending along the electrode head assembly and the lead body;

a third conductor extending within a third lead body lumen of the plurality of lead body lumens; and an attachment member coupling the third electrode and the third conductor and transferring traction forces applied to the lead body to the electrode head assembly.

2. The medical electrical lead system of claim 1, wherein the insulating member is formed of a polymer having a high dielectric strength.

3. The medical electrical lead system of claim 2, wherein the insulating member is formed of PTFE tubing.

4. The medical electrical lead system of claim 1, wherein the attachment member includes a receiving portion having an attachment member lumen receiving the third conductor, and the electrode head assembly includes a recess retaining the attachment member.

5. The medical electrical lead system of claim 4, wherein the receiving portion is one of either crimped, staked, welded or brazed to mechanically and electrically coupled the third conductor to the attachment member.

6. The medical electrical lead system of claim 4, wherein the attachment member includes a cross-groove receiving one or more coils of the third electrode.

7. The medical electrical lead system of claim 6, wherein the third electrode is welded or brazed within the cross-groove to couple the third electrode to the attachment member.

8. The medical electrical lead system of claim 6, wherein the cross-groove is compressed about the third electrode to couple the third electrode to the attachment member.

9. The medical electrical lead system of claim 4, wherein the attachment member is retained within the recess by a biocompatible plastic tube surrounding the electrode head assembly.

10. The medical electrical lead system of claim 4, wherein the electrode head assembly includes a second recess retaining the second conductor.

11. The medical electrical lead system of claim 1, wherein the drive shaft and the engaging member are machined as a single component.

12. The medical electrical lead system of claim 1, wherein the electrode head assembly houses the engaging member and the retraction flange, and the retraction flange and the electrode head assembly are formed as a single molded component.

13. The medical electrical lead system of claim 1, wherein the drive shaft includes a distal stem coupling the drive shaft to the first electrode, and wherein the retraction stop mechanism is positioned proximal to the stem to enable inspection of the coupling.

* * * * *